(12) United States Patent
Vincent et al.

(10) Patent No.: US 11,300,119 B1
(45) Date of Patent: Apr. 12, 2022

(54) SYSTEM FOR DRIVING A PULSATILE FLUID PUMP

(71) Applicant: VentriFlo, Inc., Pelham, NH (US)

(72) Inventors: Douglas E. Vincent, Pelham, NH (US); Brian Bailey, Chelmsford, MA (US); Conrad Bzura, Melrose, MA (US); David Olney, Chester, NH (US); Eric Smith, Newburyport, MA (US); Jeffrey P. Naber, Mont Vernon, NH (US); Judy Labonté, Hudson, NH (US); Kathleen Vincent, Pelham, NH (US); Matthew J. Murphy, Marshfield, MA (US); Patrick Shields, Westford, MA (US)

(73) Assignee: VentriFlo, Inc., Pelham, NH (US)

( * ) Notice: Subject to any disclaimer, the term of this patent is extended or adjusted under 35 U.S.C. 154(b) by 0 days.

(21) Appl. No.: 17/183,067

(22) Filed: Feb. 23, 2021

(51) Int. Cl.
   *F04B 43/02* (2006.01)
   *F04B 17/03* (2006.01)
   (Continued)

(52) U.S. Cl.
   CPC ......... *F04B 49/065* (2013.01); *A61M 60/178* (2021.01); *A61M 60/247* (2021.01); *A61M 60/457* (2021.01); *A61M 60/546* (2021.01); *A61M 60/585* (2021.01); *A61M 60/894* (2021.01); *F04B 17/03* (2013.01);
   (Continued)

(58) Field of Classification Search
   CPC ........ F04B 17/03; F04B 43/02; F04B 49/065; A61M 60/178; A61M 60/247; A61M 60/585
   See application file for complete search history.

(56) References Cited

U.S. PATENT DOCUMENTS

| | | | |
|---|---|---|---|
| 5,820,579 A | * | 10/1998 | Plotkin ............... A61M 1/3667 604/5.01 |
| 7,850,593 B2 | * | 12/2010 | Vincent ............... A61M 60/148 600/16 |

(Continued)

OTHER PUBLICATIONS

International Searching Authority—International Search Report, pertaining to International Application No. PCT/US2021/019262, dated Nov. 10, 2021, together with the Written Opinion of the International Searching Authority, 14 pages.

*Primary Examiner* — Patrick Hamo
(74) *Attorney, Agent, or Firm* — Sunstein LLP

(57) ABSTRACT

A pulsatile fluid pump system for driving a fluid pump assembly includes a reciprocating linear motor having a magnet and a coil, the magnet moving in relation to the coil, the coil having an electrical input. The pulsatile fluid pump system further includes a controller system having an electrical output coupled to the electrical input of the coil, and the controller system is configured to execute a waveform program defining an electrical waveform at the electrical output. The waveform program is configured to control operation of the linear motor by modification of a feature, selected from the group consisting of amplitude, frequency, shape, and combinations thereof, of the electrical waveform at the electrical output. The waveform program is further configured to accept a set of user-specifiable parameters defining the performance of the linear motor and to modify the electrical waveform in response to such parameters.

9 Claims, 8 Drawing Sheets

(51) Int. Cl.
*F04B 49/06* (2006.01)
*A61M 60/247* (2021.01)
*A61M 60/546* (2021.01)
*A61M 60/894* (2021.01)
*A61M 60/585* (2021.01)
*A61M 60/457* (2021.01)
*A61M 60/178* (2021.01)
*F04B 43/09* (2006.01)

(52) U.S. Cl.
CPC .............. *F04B 43/02* (2013.01); *F04B 43/09* (2013.01); *A61M 2205/3334* (2013.01); *A61M 2205/505* (2013.01)

(56) References Cited

U.S. PATENT DOCUMENTS

| | | | |
|---|---|---|---|
| 2002/0085952 A1* | 7/2002 | Ellingboe | A61M 1/3632 422/45 |
| 2004/0015042 A1* | 1/2004 | Vincent | A61M 60/40 600/17 |
| 2012/0042192 A1* | 2/2012 | Rae | H03B 5/04 713/500 |
| 2012/0245405 A1 | 9/2012 | Tatum et al. | |
| 2015/0078934 A1 | 3/2015 | Lucas | |
| 2018/0230997 A1* | 8/2018 | Dearden | F04C 2/18 |
| 2020/0289731 A1 | 9/2020 | Scheffler et al. | |

* cited by examiner

SYSTEM FOR DRIVING A PULSATILE FLUID PUMP

RELATED APPLICATIONS

The present application is one of four applications being filed on the same day and bearing U.S. Ser. Nos. 17/182,915, 17/182,893, 17/183,067, and 17/183,080. Each of these related applications, other than the present application, is hereby incorporated herein by reference in its entirety.

TECHNICAL FIELD

The present invention relates to pulsatile fluid pumps, and more particularly to pulsatile fluid pumps suitable for pumping blood.

BACKGROUND ART

A pulsatile fluid pump is taught in U.S. Pat. No. 7,850,593 ("our prior patent") for an invention of Douglas Vincent and Matthew Murphy, who are co-inventors of the present invention. Our prior patent discloses a pump actuated by a linear motor configured to cause reciprocation of a flexible membrane, serving as a wall of a fluid housing, that is in turn coupled to a pair of ball valves, in a manner as to implement pulsatile fluid flow.

SUMMARY OF THE EMBODIMENTS

In accordance with one embodiment of the invention, a pulsatile fluid pump system for driving a fluid pump assembly includes a reciprocating linear motor having a magnet and a coil, the magnet moving in relation to the coil, the coil having an electrical input. The pulsatile fluid pump system further includes a controller system having an electrical output coupled to the electrical input of the coil, and the controller system is configured to execute a waveform program defining an electrical waveform at the electrical output. The waveform program is configured to control operation of the linear motor by modification of a feature, selected from the group consisting of amplitude, frequency, shape, and combinations thereof, of the electrical waveform at the electrical output. The waveform program is further configured to accept a set of user-specifiable parameters defining the performance of the linear motor and to modify the electrical waveform in response to such parameters.

Alternatively or in addition, the pulsatile fluid pump system further includes a graphic display, coupled to the controller system, the controller system executing a graphics program configured to cause the graphic display to show a set of user-specifiable parameters defining the performance of the linear motor.

Alternatively or in addition, the pulsatile fluid pump system further includes a flow sensor mechanically coupled to a fluid path including the integrated pump assembly, the flow sensor having an electrical output coupled to the controller system, wherein the controller system is executing a graphics program configured to cause the graphic display to show a set of items, including values of a set of user-specifiable parameters defining the performance of the linear motor and values of a set of physical flow characteristics.

Also alternatively or in addition, the set of items shown includes an instantaneous flow rate waveform in near real-time. Alternatively or in addition, the set of items shown includes an instantaneous stroke volume waveform in near real-time.

Also alternatively or in addition, the waveform program is configured to generate the electrical waveform at the electrical output by repeatedly performing a multi-piece polynomial spline algorithm in a manner responsive to a set of user-specifiable parameters defining the performance of the linear motor.

In a related embodiment, the controller system has a storage system in which is stored an archetype electrical waveform, and the waveform program reads the archetype electrical waveform from the storage system and modifies the archetype electrical waveform, based upon a set of user-specifiable parameters defining the performance of the linear motor, to generate the electrical waveform at the electrical output.

Alternatively or in addition, the pulsatile fluid pump system further includes a set of sensors, electrically coupled to the controller system and configured to produce a set of sensor outputs corresponding to pumping performance. The waveform program is configured to generate the electrical waveform at the electrical output in a manner responsive to the set of sensor outputs and a set of user-specifiable parameters.

Also alternatively or in addition, the user of the pulsatile fluid pump system may choose from a set of waveform programs. Alternatively or in addition, the graphic display is touch sensitive.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

Figure 1:
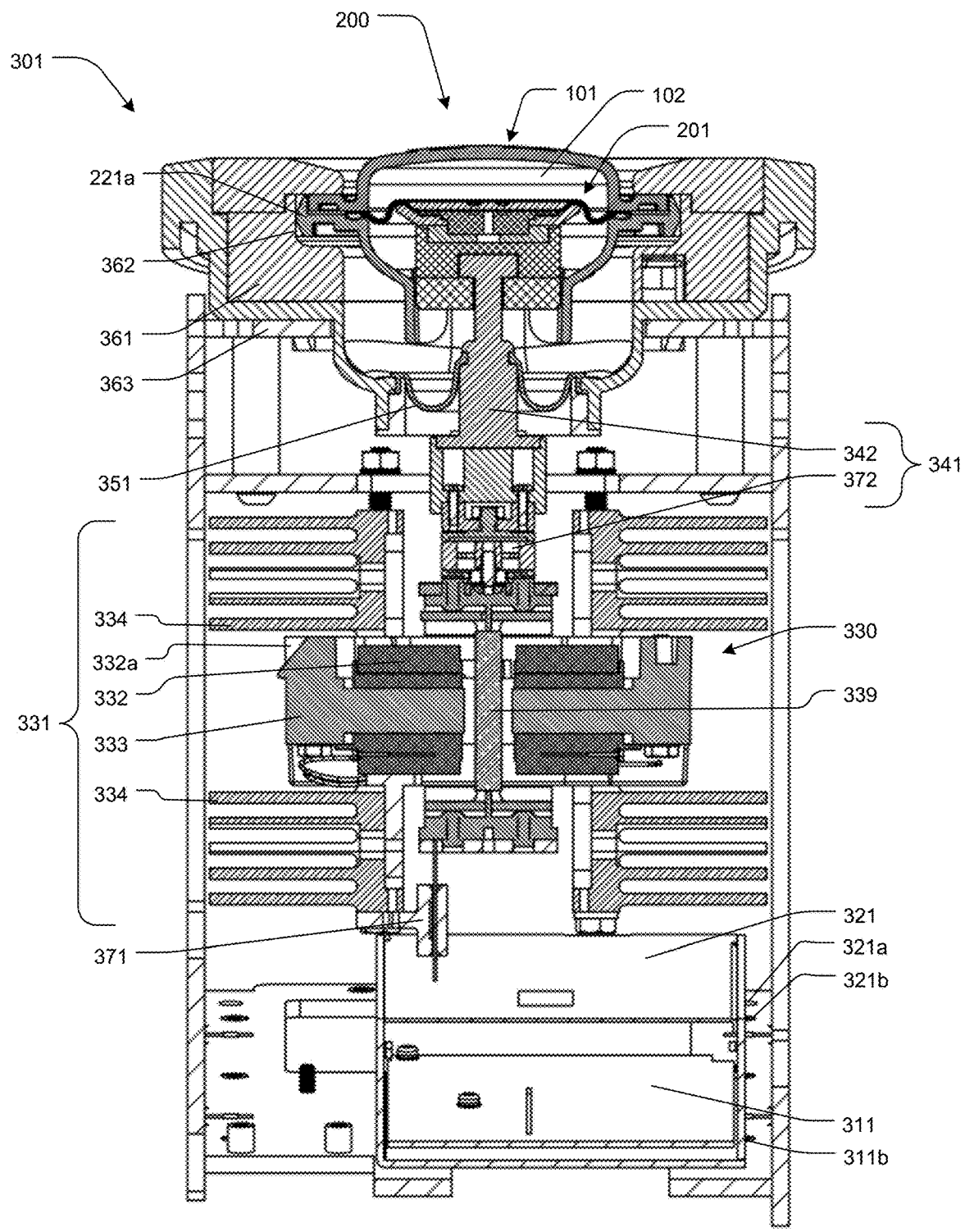
FIG. 1 is a vertical section of the pulsatile fluid pump system 301 showing the controller system 311, power amplifier 321, linear motor 330 (coil 332, cooling fins 334, and magnet 339), push rod assembly 341, flexible seal 351, control housing 361, and the integral pump assembly 200.

Definitions. As used in this description and the accompanying claims, the following terms shall have the meanings indicated, unless the context otherwise requires:

A "set" includes at least one member.

An "electrical waveform" is a waveform selected from the group consisting of an electrical current waveform, a voltage waveform, and combinations thereof.

The term "user-specifiable input parameter" includes a user-definable attribute pertinent to an alarm setting or calculation for a user interface, such as low flow limit 421a, high flow limit 421b, and body surface area 421c (BSA), as well as combinations of any of the foregoing attributes.

The term "user-specifiable parameter defining the performance of the linear motor" in the course of pumping includes a motor performance attribute such as stroke strength 401a, beat rate 401b, flow rate, average flow rate, stroke volume, flow index, pulse pressure, output pressure, magnet displacement, as well as combinations of any of the foregoing attributes.

The term "physical flow characteristic" includes a measured attribute such as stroke strength, beat rate, flow rate, average flow rate 411a, stroke volume 411b, flow index 411c, pulse pressure, flow rate waveform 412, stroke volume waveform 413, duration over which the pump has been running (e.g., measured by timer 414), as well as combinations of any of the foregoing attributes. If an attribute is user-specified in a given embodiment of the present invention, then measurement of the attribute is of subsidiary importance since its value has been specified. Similarly, if an attribute being measured has primary importance in a given embodiment of the present invention, then the parameter would not have been user-specified.

Figure 4:
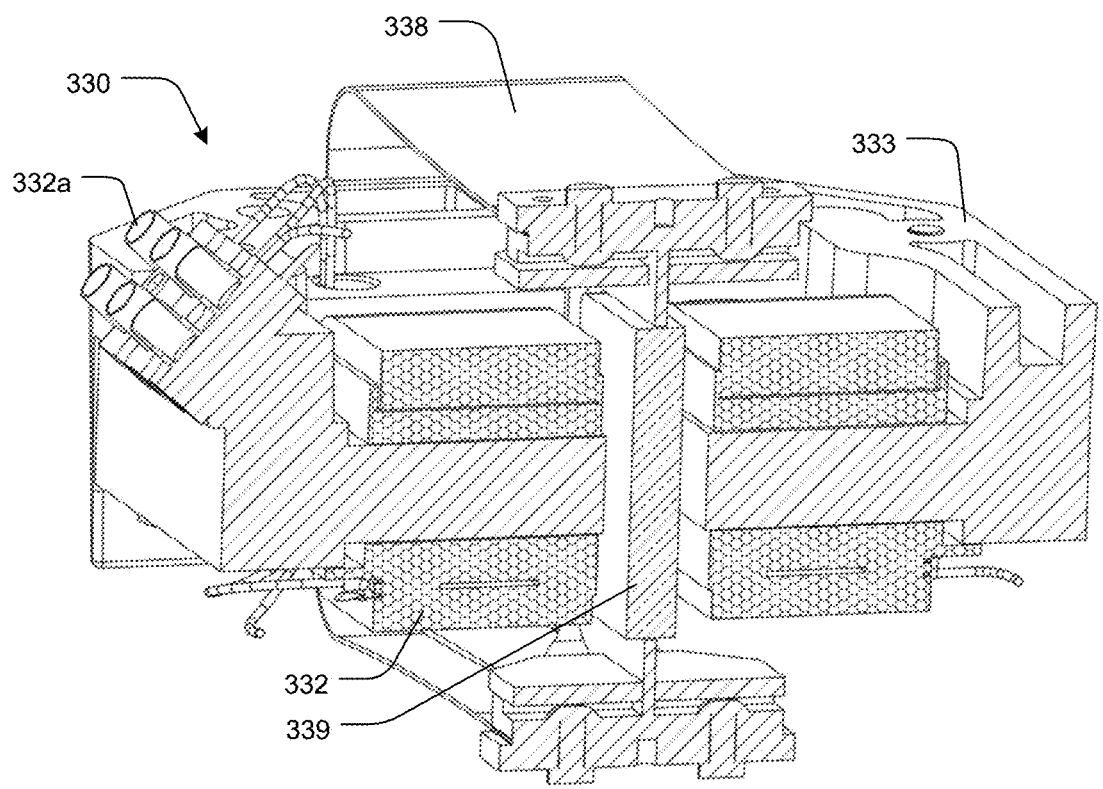
FIG. 4 is a vertical section of the linear motor 330.

FIG. 1 is a vertical section of the pulsatile fluid pump system 301 showing the controller system 311 (with electrical output 311b), power amplifier 321 (with electrical input 321a and electrical output 321b), linear motor 330 (comprised of a stationary member 331 which includes a coil 332 [with electrical input 332a], a frame 333, and cooling fins 334, and a moving member which includes a spring 338 of FIG. 4 and a magnet 339), position sensor 371, push rod assembly 341 (comprised of a push rod 342 and force sensor 372), flexible seal 351, control housing 361, and chassis 363. An integral pump assembly 200 (comprised of the pump-valving assembly 101 with chamber 102, diaphragm assembly 201, and peripheral flange 221a) is held by the peripheral flange 221a and compliant member (not shown) in the channel 362 within the control housing 361. (In these figures, like numbered items correspond to similar components across different figures.)

Figure 2:
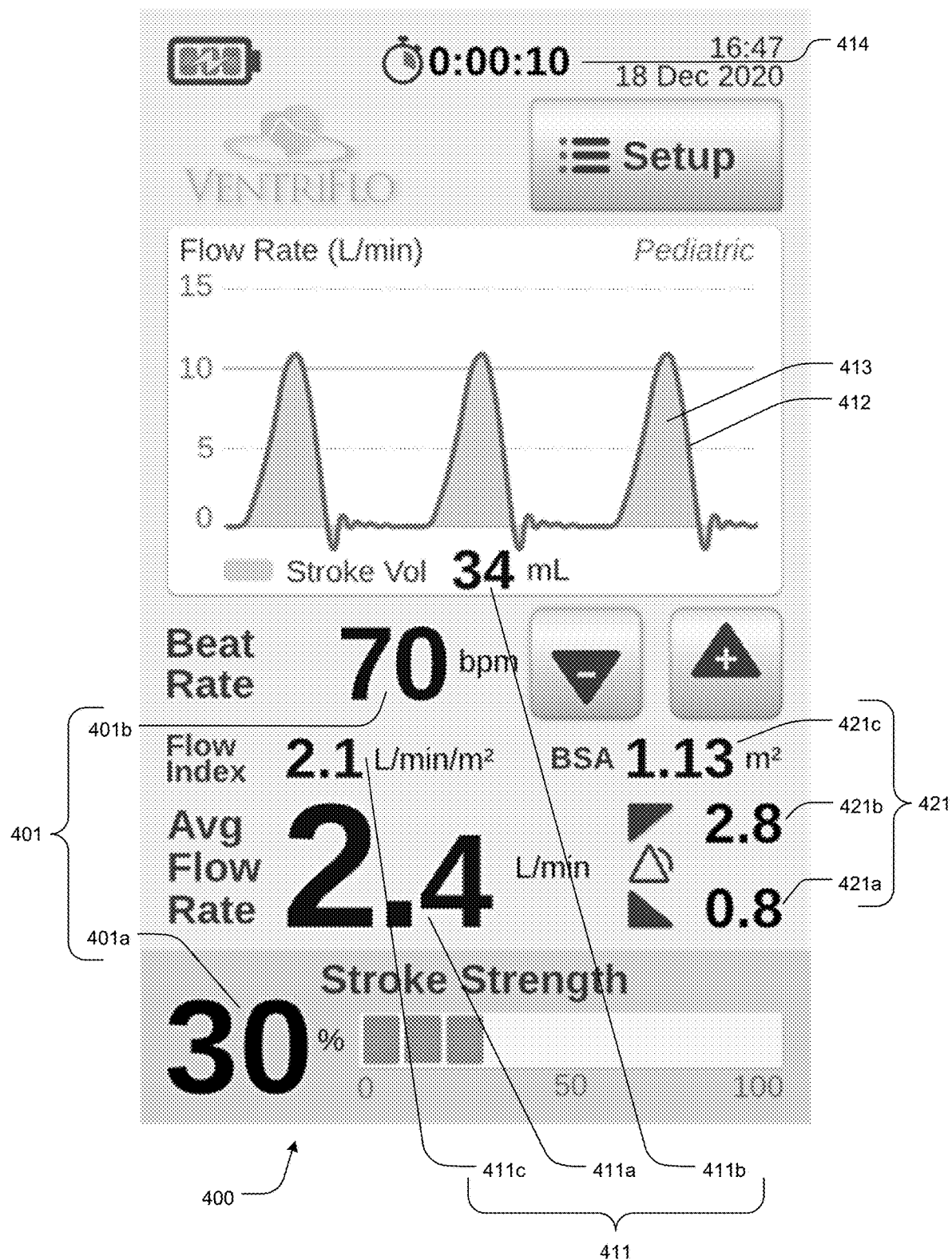
FIG. 2 is an example of the touch-sensitive graphic display 400 user interface showing the user-specifiable motor parameters 401, flow characteristics 411, and user-specifiable input parameters 421.

FIG. 2 is an example of a touch-sensitive graphic display 400 user interface showing user-specifiable motor parameters 401. In this interface appear parameters stroke strength 401a and beat rate 401b. These parameters are a subset of user-specifiable parameters defining the performance of the linear motor. Additionally, in this interface appear flow characteristics 411 (average flow rate 411a, stroke volume 411b, flow index 411c), flow rate waveform 412, stroke volume waveform 413, and timer 414. These flow-based attributes are a subset of physical flow characteristics. Additionally, the user interface displays user-specifiable inputs 421 (low flow limit 421a, high flow limit 421b, and body surface area 421c).

Figure 3:
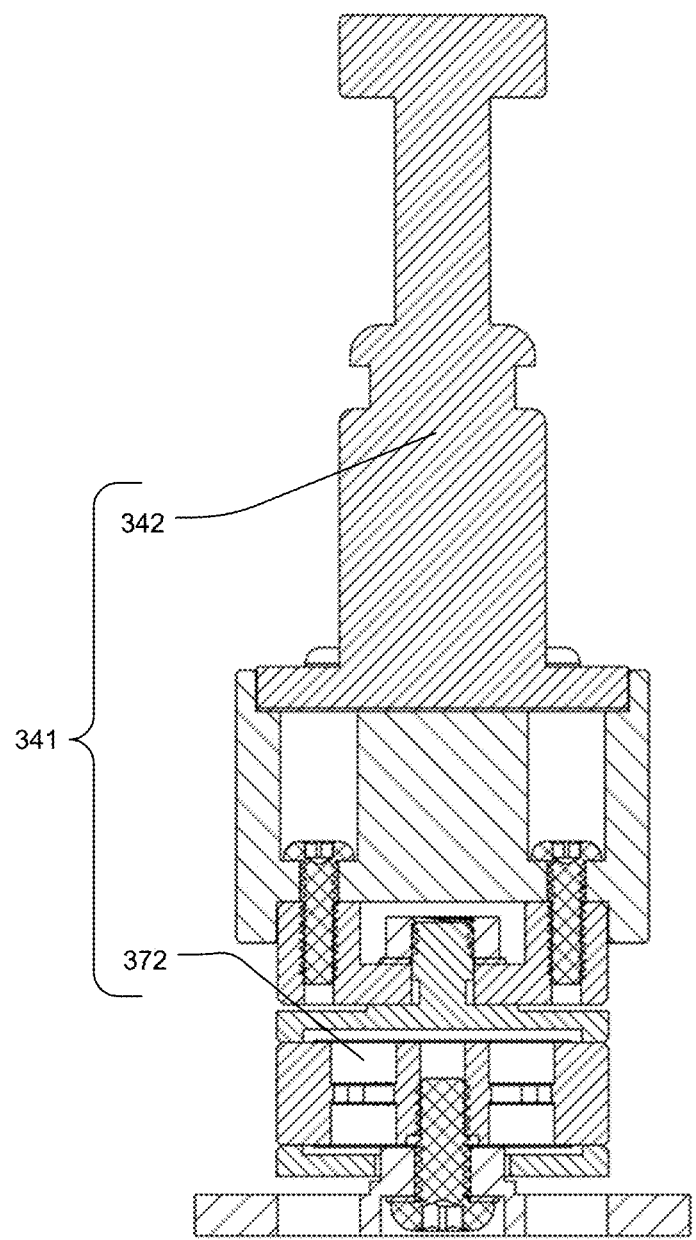
FIG. 3 is a vertical section of the push rod assembly 341.

FIG. 3 is a vertical section of the push rod assembly 341 comprised of a push rod 342 and force sensor 372.

FIG. 4 is a vertical section of the linear motor 330, showing the coil 332 with electrical input 332a, the frame 333, the magnet centering spring 338, and the magnet 339. Other components and detail of the motor are provided in FIG. 1.

Figure 5:
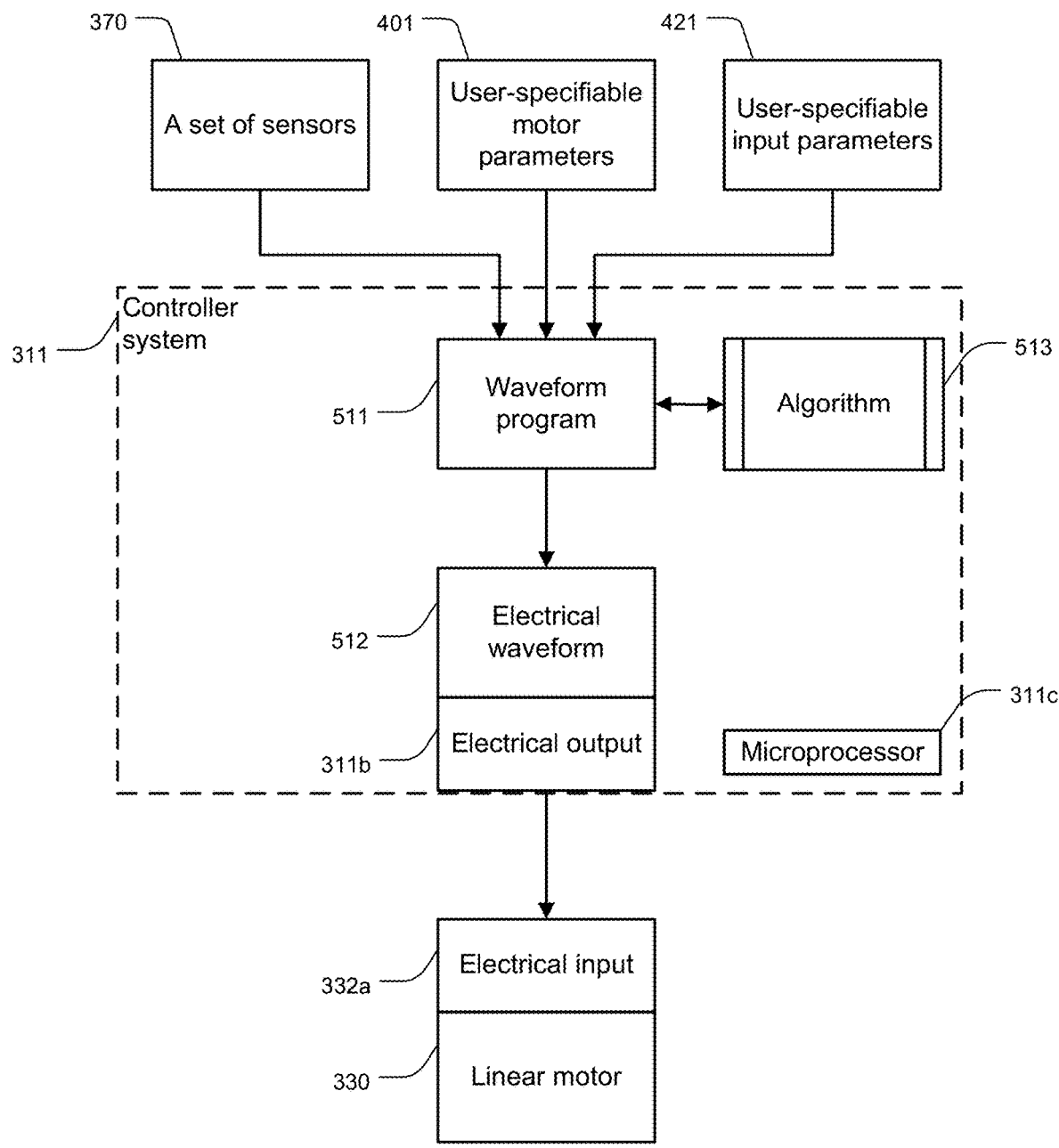
FIG. 5 is a block diagram describing a waveform program

In FIG. 5, the waveform program 511 is a computer program executed by the controller system 311 microprocessor 311c which accepts input from a set of sensors 370 (including position sensor 371 of FIG. 1, force sensor 372 of FIGS. 1 and 3, and an external flow sensor 373 of FIG. 8), a set of user-specifiable motor parameters 401 (stroke strength 401a and beat rate 401b) defining performance of a linear motor 330 in the course of pumping. Additionally, FIG. 5 shows a set of user-specifiable input parameters 421 (low flow limit 421a, high flow limit 421b, and body surface area 421c). The waveform program 511 outputs an electrical waveform 512, the result of a set of algorithms 513, at the electrical output 311b. The electrical output 311b is coupled to electrical input 332a of linear motor 330.

There is growing consensus that desirable characteristics of a pulsatile pump should include both sufficient hemodynamic energy and a human-like waveform architecture. To evaluate pulsatile flow, we choose the human heart as the best model: it delivers a proper stroke volume at a natural cadence with a physiologic rest at the end of each stroke, adapting to the physiologic demands of the patient by adjusting the cardiac output, as the product of stroke volume and beat rate. Via the left ventricle, the human heart provides hemodynamic energy that results in a pressure wave that propagates fully through the elastic arterial tree. It appears that only a biomimetic stroke volume delivered in a biomimetic time frame (like the native systolic contraction produced by the heart) allows the elastic arterial tree to properly relax during the diastolic phase. Use of continuous flow devices stretches the elastic arterial wall but never allows proper relaxation, creating constant and atypical stress on the endothelial cells and interfering with natural baroreceptor sympathetic and parasympathetic signaling, thus disrupting the body's homeostatic control state.

The waveform program 511 causes the pulsatile fluid pump system 301 to replicate the ability of the left ventricle of the human heart to deliver physiological hemodynamic energy proportional to a user-specified stroke strength 401a by causing delivery of the necessary fraction of the stroke volume of a pump chamber 102 in a physiologic natural cadence at a user-specified beat rate 401b. It is a user (a perfusionist) of the pulsatile fluid pump system 301 who adjusts the stroke strength 401a (an indirect specification of stroke volume) and beat rate 401b to meet the physiologic demand of the patient. Furthermore, the waveform program 511 replicates the physiologic rest at the end of each stroke, thereby allowing natural relaxation of the arterial tree.

The structure of a pulsatile pump in accordance with various embodiments of the present invention can usefully reflect attributes of the human heart. The human heart is preload sensitive—the heart cannot "pull" blood into the left ventricle; it can only allow the blood available to flow naturally into the ventricle. The human heart is also afterload sensitive in that it is responsive to the compliance and resistance in the downstream vasculature and doesn't exert excess force on the blood, which could damage the vasculature. Lastly, the left ventricle cannot deliver blood that isn't in the ventricle when it contracts; there is a limited bolus of blood that it can deliver.

The pulsatile fluid pump system 301 has similar attributes of inherent safety: it is preload and afterload sensitive, and it is limited in both the volume of blood it can deliver and the force at which it can deliver that bolus of blood. When filling, the pulsatile fluid pump system 301 allows gravity filling from the venous reservoir, exerting minimal negative pressure. When emptying, the linear motor 330 is inherently limited in the force that it can generate by its design. As such, it cannot overpressure the downstream tubing or vasculature, instead delivering less than the volume of blood in the pump chamber 102, thereby only delivering as much volume as the vasculature can receive.

The integral pump assembly 200 is analogous to a left ventricle of the human heart; the inlet ball check valve assembly used in various embodiments hereof is analogous to a mitral valve; and the outlet ball check valve assembly used in various embodiments hereof is analogous to an aortic valve. Like the human heart, the inlet and outlet ball check valve assemblies are passive and require a slight reversal of flow to close. This slight reversal of flow mimics the slight reversal that occurs when the aortic valve of the human heart closes.

Figure 6:
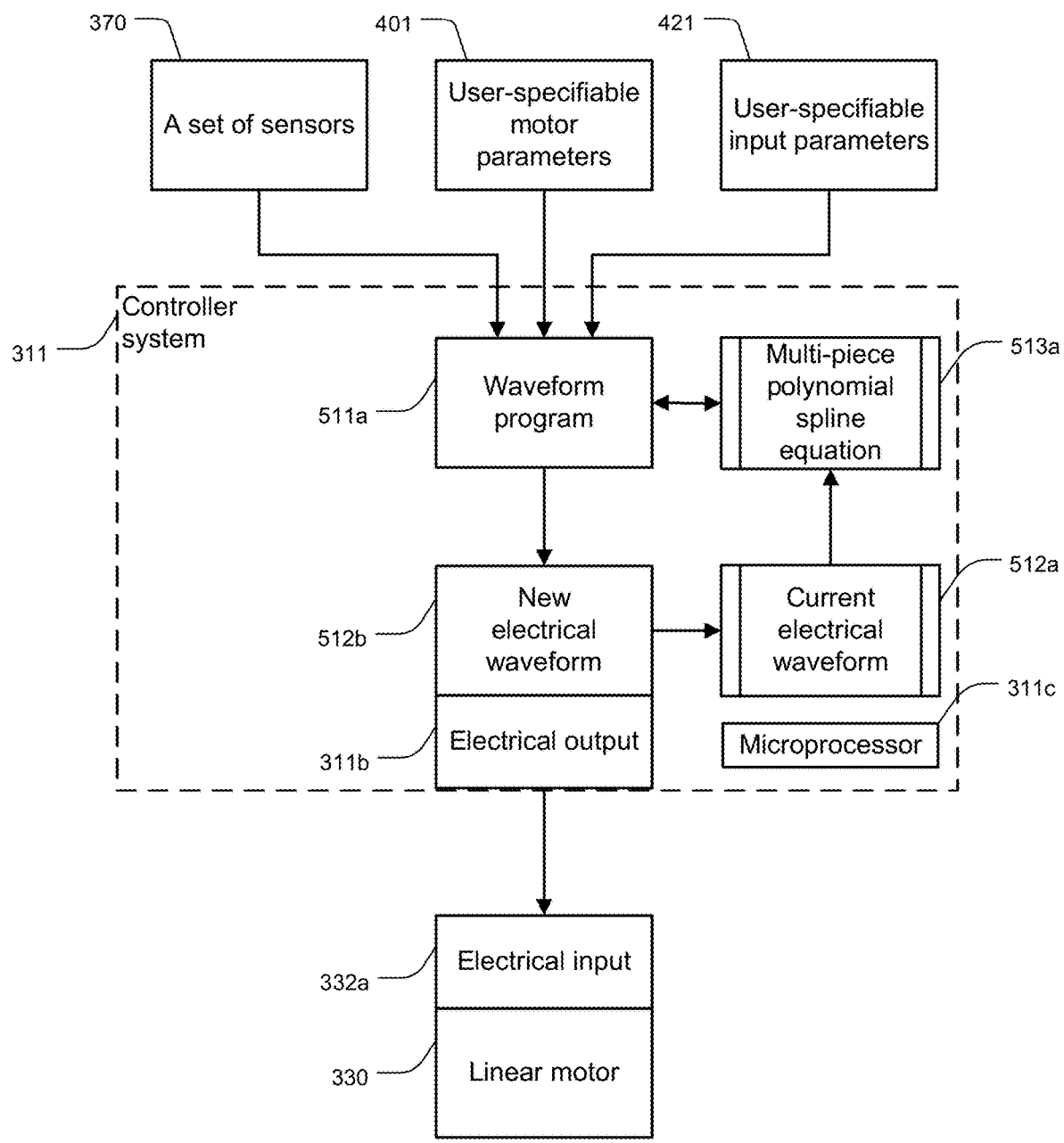
FIG. 6 is a block diagram describing a first embodiment 511a of the waveform program 511.

In one embodiment of the present invention, shown in FIG. 6, the waveform program 511a is a computer program executed by the controller system 311 microprocessor 311c which accepts input from a set of sensors 370, a set of user-specifiable motor parameters 401, and a set of user-specifiable input parameters 421. The waveform program 511a is configured to simulate a waveform that has been experimentally determined to be appropriate for embodiments of the pulsatile fluid pump system 301 of the present invention. The waveform program 511a simulates the experimentally determined waveform by repeatedly performing a multi-piece polynomial spline algorithm 513a and the resulting waveform is used to drive the linear motor 330. In the event that the user changes one of the user-specifiable motor parameters 401, the waveform program 511a uses zero or more of the current and/or previous values from the set of sensors 370, along with the set of user-specifiable motor parameters 401, zero or more flow characteristics 411, zero or more user-specifiable input parameters 421, and the current electrical waveform 512a to create a new electrical waveform 512b. The waveform program 511a outputs the new electrical waveform 512b, consisting of discrete output voltages at defined time durations, at the electrical output 311b. The electrical output 311b is coupled to electrical input 332a of linear motor 330.

Figure 7:
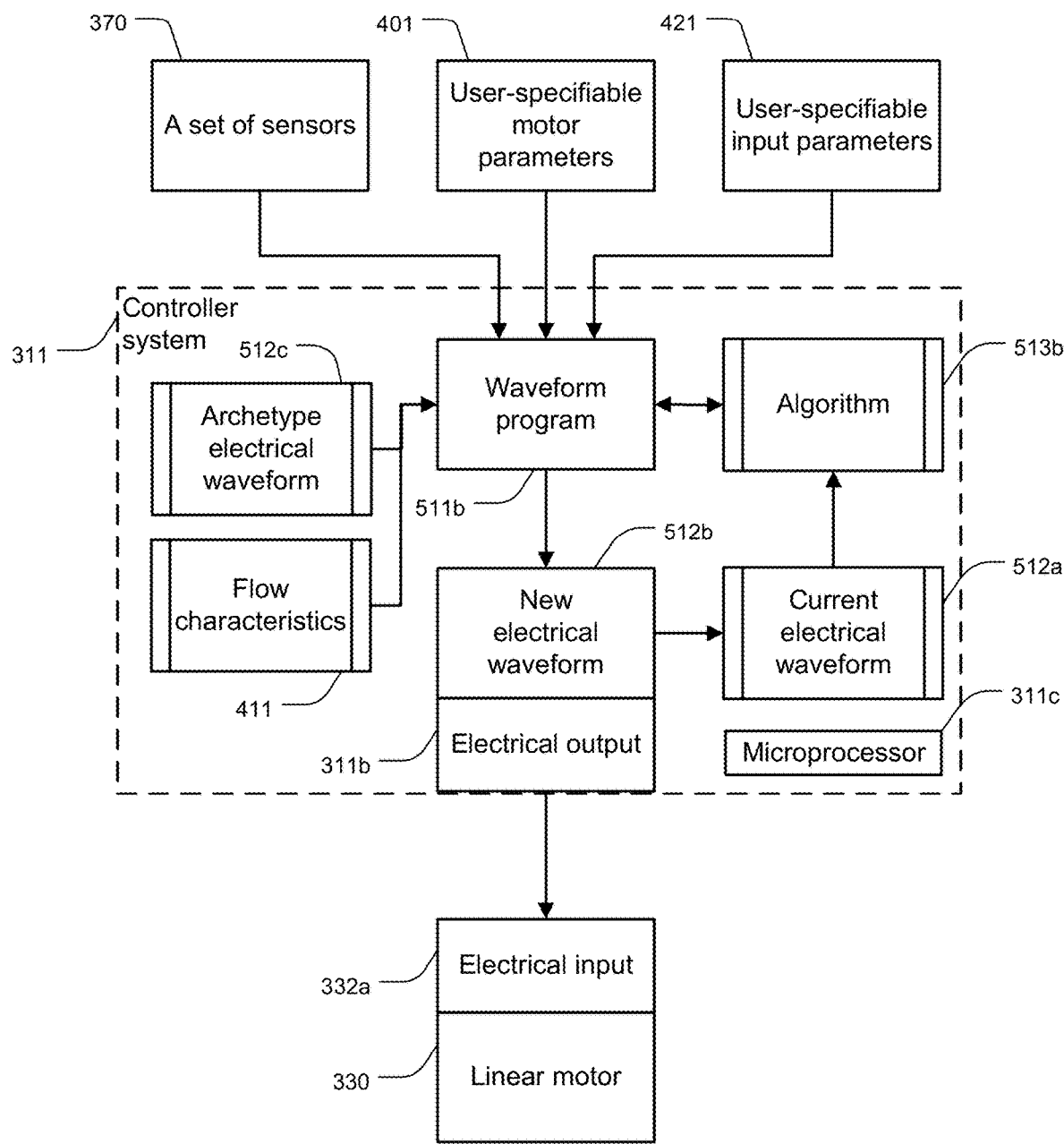
FIG. 7 is a block diagram describing a second embodiment 511b of the waveform program 511.

In another embodiment of the present invention, shown in FIG. 7, the waveform program 511b is a computer program executed by the controller system 311 microprocessor 311c which accepts input from a set of sensors 370, a set of user-specifiable motor parameters 401, and a set of user-specifiable input parameters 421. The waveform program 511b reads an archetype electrical waveform 512c stored electronically within the controller system 311. The waveform program 511b then uses an algorithm 513b to adjust the archetype electrical waveform 512c. The algorithm 513b creates a new electrical waveform 512b from the archetype electrical waveform 512c using zero or more of the current and/or previous values of the set of sensors 370, along with the set of user-specifiable motor parameters 401, zero or more flow characteristics 411, zero or more user-specifiable input parameters 421, and the current electrical waveform 512a. The waveform program 511b outputs the new electrical waveform 512b, consisting of discrete output voltages at defined time durations, at the electrical output 311b. The electrical output 311b is coupled to electrical input 332a of linear motor 330.

Figure 8:
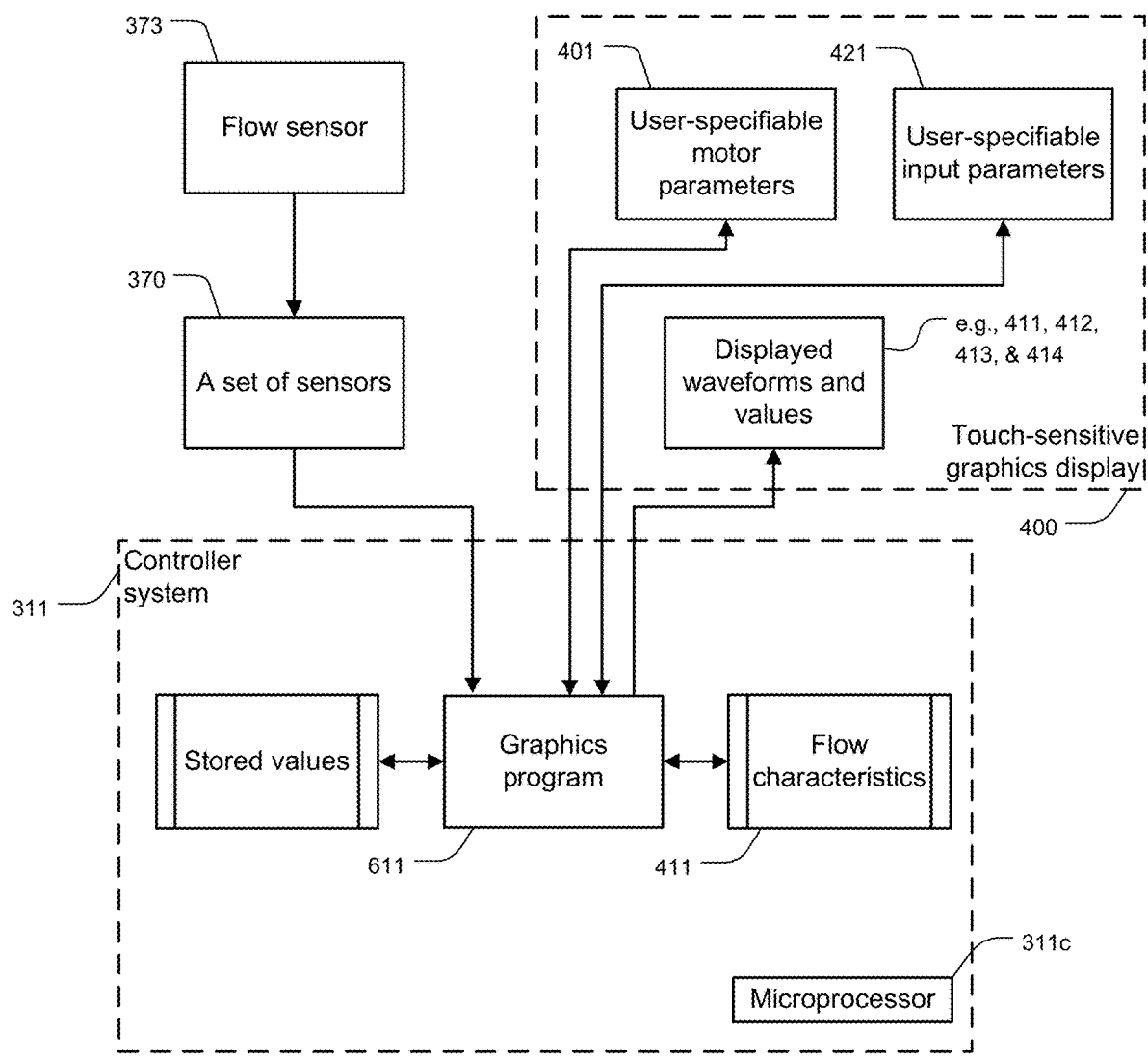
FIG. 8 is a block diagram describing a graphics program 611.

In FIG. 8, the graphics program 611 is a computer program executed by the controller system 311, which accepts user-specifiable motor parameters 401 and user-specifiable input parameters 421. The graphics program 611 causes a set of current values of the user-specifiable motor parameters 401, a set of flow characteristics 411, and a set of user-specifiable input parameters 421 to be shown on the graphic display 400.

When the stroke strength 401a value transitions from zero to a positive value, the graphics program 611 sets timer 414 to zero, increments the timer 414 in real time, and causes, each second, the updated timer 414 value to be shown on the graphic display 400. When the stroke strength 401a value transitions from a positive value to zero, the graphics program 611 stops incrementing the timer 414 and causes the most recent value of timer 414 to be shown on the graphic display 400.

The graphics program 611 accepts input from the flow sensor 373, calculates the average flow rate 411a, and causes the average flow rate 411a to be shown on the graphic display 400. The graphics program 611 also causes, in near real-time, the instantaneous flow rate as a flow rate waveform 412 to be shown on the graphic display 400.

The graphics program 611 also uses data from the flow sensor 373 to calculate the average stroke volume 411b and cause the average stroke volume 411b to be shown on the graphic display 400. The graphics program 611 also causes, in near real-time, the total volume of fluid currently delivered for a given stroke to be shown on the graphic display 400. The total volume of fluid currently delivered for a given stroke is the integral of instantaneous flow as a stroke volume waveform 413 and is displayed as the shaded area under the flow rate waveform 412.

The graphics program 611 accepts input of body surface area 421c and calculates flow index 411c as the average flow rate 411a divided by the body surface area 421c. The graphics program 611 further causes the body surface area 421c and calculated flow index 411c to be shown on the graphic display 400.

The graphics program 611 accepts input of low flow limit 421a and high flow limit 421b, and causes the low flow limit 421a and high flow limit 421b settings to be shown on the graphic display 400.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A pulsatile fluid pump system for driving a fluid pump assembly, the pulsatile fluid pump system comprising:
   a reciprocating linear motor having a magnet and a coil, the magnet moving in relation to the coil, the coil having an electrical input;
   a controller system having an electrical output coupled to the electrical input of the coil and a storage system in which is stored an archetype electrical waveform, the controller system being configured to execute a waveform program defining an electrical waveform at the electrical output;
   wherein the waveform program is configured to accept user-provided values of a set of user-specifiable parameters defining performance of the linear motor and further configured to read the archetype electrical waveform from the storage system and to generate the electrical waveform at the electrical output by modifying the archetype electrical waveform with respect to a feature, selected from the group consisting of amplitude, frequency, shape, and combinations thereof, in response to the user-provided values for such parameters.

2. A pulsatile fluid pump system according to claim 1, further comprising a graphic display, coupled to the controller system, the controller system executing a graphics program configured to cause the graphic display to show the user-provided values of the set of user-specifiable parameters defining the performance of the linear motor.

3. A pulsatile fluid pump system according to claim 2, further comprising a flow sensor mechanically coupled to a fluid path including the integrated pump assembly, the flow sensor having an electrical output coupled to the controller system, wherein the controller system is executing a graphics program configured to cause the graphic display to show a set of items, including values of a set of physical flow characteristics.

4. A pulsatile fluid pump system according to claim 3, wherein the set of items shown includes an instantaneous flow rate waveform in near real-time.

5. A pulsatile fluid pump system according to claim 3, wherein the set of items shown includes an instantaneous stroke volume waveform in near real-time.

6. A pulsatile fluid pump system according to claim 1, wherein the waveform program is configured to generate the electrical waveform at the electrical output by repeatedly performing a multi-piece polynomial spline algorithm in a manner responsive to the user-provided values of the set of user-specifiable parameters defining the performance of the linear motor.

7. A pulsatile fluid pump system according to claim 1, further comprising a set of sensors, electrically coupled to the controller system and configured to produce a set of sensor outputs corresponding to pumping performance, wherein the waveform program is configured to generate the electrical waveform at the electrical output in a manner responsive to the set of sensor outputs and the user-provided values of the set of user-specifiable parameters.

8. A pulsatile fluid pump system according to claim 1, wherein the user of the pulsatile fluid pump system may choose from a set of waveform programs.

9. A pulsatile fluid pump system according to claim 2, wherein the graphic display is touch sensitive.

* * * * *